United States Patent
Xu et al.

(10) Patent No.: US 11,497,500 B2
(45) Date of Patent: Nov. 15, 2022

(54) SURGICAL INSTRUMENT AND LINEAR STAPLER

(71) Applicant: Suzhou Intocare Medical Technology Co., Ltd, Jiangsu (CN)

(72) Inventors: Ronghua Xu, Jiangsu (CN); Hui Zhang, Jiangsu (CN); Yunfeng Du, Jiangsu (CN); Dianchen Liu, Jiangsu (CN)

(73) Assignee: INTOCARE MEDICAL TECHNOLOGY (SUZHOU) CO., LTD, Jiangsu (CN)

( * ) Notice: Subject to any disclaimer, the term of this patent is extended or adjusted under 35 U.S.C. 154(b) by 34 days.

(21) Appl. No.: 17/273,057

(22) PCT Filed: Nov. 14, 2019

(86) PCT No.: PCT/CN2019/118383
§ 371 (c)(1),
(2) Date: Mar. 3, 2021

(87) PCT Pub. No.: WO2020/151334
PCT Pub. Date: Jul. 30, 2020

(65) Prior Publication Data
US 2021/0322008 A1    Oct. 21, 2021

(30) Foreign Application Priority Data

Jan. 24, 2019 (CN) .......................... 201910067866.7

(51) Int. Cl.
*A61B 17/072* (2006.01)
*A61B 17/00* (2006.01)

(52) U.S. Cl.
CPC .................. *A61B 17/07207* (2013.01); *A61B 2017/00017* (2013.01); *A61B 2017/00398* (2013.01);
(Continued)

(58) Field of Classification Search
CPC .... A61B 2017/07257; A61B 17/07207; A61B 17/072
See application file for complete search history.

(56) References Cited

U.S. PATENT DOCUMENTS 7,766,207 B2 * 8/2010 Mather ................ A61B 17/072
227/181.1
7,954,685 B2 * 6/2011 Viola ................... A61B 17/068
227/19
(Continued)

FOREIGN PATENT DOCUMENTS

CN           105476678 A     4/2016
CN           106388893 A     2/2017
(Continued)

OTHER PUBLICATIONS

EP Search Report dated Oct. 8, 2021 in EP application (No. 19911959.5-1122/3834742).

*Primary Examiner* — Hemant Desai
*Assistant Examiner* — Andrew C Ardolino
(74) *Attorney, Agent, or Firm* — McClure, Qualey & Rodack, LLP (57) ABSTRACT

A surgical instrument and a linear surgical stapler are provided. The instrument includes: a suturing mechanism including an anvil assembly and a mounting part for mounting a staple cartridge assembly, in which the staple cartridge assembly includes a staple cartridge for accommodating staples, and the anvil assembly includes an anvil matched with the staple cartridge; a staple pushing assembly, configured to push the staples so that the staples are sequentially fired; a transmission assembly, configured for driving the staple cartridge assembly to move relative to the anvil assembly and driving the staple pushing assembly to move (Continued)

to push the staples; and a drive assembly, connected to the transmission assembly and configured for driving the transmission assembly to move.

13 Claims, 5 Drawing Sheets

(52) U.S. Cl.
 CPC ............ *A61B 2017/00681* (2013.01); *A61B 2017/07257* (2013.01); *A61B 2017/07271* (2013.01)

(56) References Cited

U.S. PATENT DOCUMENTS

| | | | | |
|---|---|---|---|---|
| 8,276,801 | B2* | 10/2012 | Zemlok | A61B 90/90 227/176.1 |
| 8,616,431 | B2* | 12/2013 | Timm | A61B 17/072 606/167 |
| 8,955,732 | B2* | 2/2015 | Zemlok | A61B 17/07207 227/176.1 |
| 9,649,110 | B2* | 5/2017 | Parihar | A61B 17/1155 |
| 10,194,913 | B2* | 2/2019 | Nalagatla | A61B 17/32 |
| 10,213,201 | B2* | 2/2019 | Shelton, IV | A61B 17/068 |
| 2001/0045442 | A1* | 11/2001 | Whitman | A61B 17/068 227/19 |
| 2002/0084304 | A1* | 7/2002 | Whitman | A61B 17/07207 227/176.1 |
| 2006/0273135 | A1* | 12/2006 | Beetel | A61B 17/128 227/175.1 |
| 2014/0021241 | A1 | 1/2014 | Marczyk et al. | |
| 2014/0239044 | A1* | 8/2014 | Hoffman | A61B 17/07207 227/176.1 |
| 2016/0270780 | A1* | 9/2016 | Hall | A61B 90/98 |
| 2017/0281189 | A1* | 10/2017 | Nalagatla | A61B 17/3211 |

FOREIGN PATENT DOCUMENTS

| | | |
|---|---|---|
| CN | 206809304 U | 12/2017 |
| CN | 107928733 A | 4/2018 |
| CN | 108135597 A | 6/2018 |
| WO | 2010054404 A1 | 5/2010 |
| WO | 2018096711 A1 | 5/2018 |

\* cited by examiner

SURGICAL INSTRUMENT AND LINEAR STAPLER

The present application claims priority of the Chinese Patent Application No. 201910067866.7 filed on Jan. 24, 2019, the disclosure of which is incorporated herein by its reference in its entirety as part of the present application.

TECHNICAL FIELD

The present disclosure relates to a surgical instrument and a linear surgical stapler, and belongs to the field of medical instruments.

BACKGROUND

A linear surgical stapler, also known as a digestive tract closer, is an instrument that insert a plurality of staples staggered each other into a target tissue in a straight line. The linear surgical stapler is one of the instruments widely used to replace a linearly manual suturing, is mainly used to suture and close the stumps of stomach, duodenum, small intestine, and colon and is a full-layer eversion suturing instrument.

A manner of inserting the staples into the target tissue by the linear surgical stapler in the prior art is usually that a transmission device pushes an anvil to push out and fire all of the staples at one time. In this case, the staples are prone to having large and small heads, a dovetail and the like so that an inserting effect is poor, resulting in a poor suturing effect and waste of staples. In addition, because a large number of staples are fired at one time, a part of the staples cannot be firmly inserted into the target tissue, resulting in tissue leakage. In addition, because a large number of staples need to be fired at one time, a relatively large firing force is needed, which causes the anvil with a cantilever beam structure to deform after a plurality of firings.

SUMMARY

The present disclosure aims to provide a surgical instrument and a linear surgical stapler, which fire the staples sequentially, and thus can reduce the firing force to avoid the deformation of the anvil, and have a better insertion effect of the staples into the tissue, a better suturing effect and surgical safety.

In order to achieve the above objects, the technical solutions of the present disclosure are provided as follows. A surgical instrument comprises: a suturing mechanism comprising an anvil assembly and a mounting part for mounting a staple cartridge assembly, in which the staple cartridge assembly comprises a staple cartridge for accommodating staples, and the anvil assembly comprises an anvil matched with the staple cartridge; a staple pushing assembly, configured to push the staples so that the staples are sequentially fired; a transmission assembly, connected to the staple cartridge assembly and the staple pushing assembly, and configured for driving the staple cartridge assembly to move relative to the anvil assembly and driving the staple pushing assembly to move; and a drive assembly, connected to the transmission assembly and configured for driving the transmission assembly to move.

For example, the staple pushing assembly comprises a first threaded rod provided on the anvil assembly and a firing nut sleeved on the first threaded rod, and an axis direction of the first threaded rod and the firing nut is defined as a first axis direction; the surgical instrument further comprises a direction-changing transmission device; and if the suturing mechanism is closed, the direction-changing transmission device connects the staple pushing assembly and the transmission assembly and drives the first threaded rod to rotate, so that the firing nut moves relative to the first threaded rod in the first axis direction.

For example, the transmission assembly comprises a transmission rod, the transmission rod is connected to the drive assembly and rotates under an action of the drive assembly, an axis direction of the transmission rod is defined as a second axis direction, and the first axis direction is perpendicular to the second axis direction.

For example, the direction-changing transmission device comprises a large bevel gear sleeved on the transmission rod and a small bevel gear sleeved on the first threaded rod; and if the suturing mechanism is closed, the large bevel gear is engaged with the small bevel gear.

For example, the transmission rod is a second threaded rod, a threaded sleeve and a sleeve are sleeved on the second threaded rod, and the sleeve is connected to the threaded sleeve and provided between the threaded sleeve and the large bevel gear; and if the drive assembly drives the second threaded rod to rotate, the threaded sleeve moves relative to the second threaded rod in the second axis direction, thereby driving the sleeve to move relative to the second threaded rod in the second axis direction.

For example, the threaded sleeve and the sleeve are integral with each other.

For example, the transmission assembly further comprises a closure assembly sleeved on the second threaded rod, the closure assembly comprises a first closure rod and a second closure rod, the threaded sleeve is fixedly connected to the first closure rod and the second closure rod, and the threaded sleeve is provided between the first closure rod and the second closure rod; the first closure rod is connected to the staple cartridge assembly, and the second closure rod is provided closer to the drive assembly than the first closure rod; and if the drive assembly drives the second threaded rod to rotate, the threaded sleeve moves relative to the second threaded rod in the second axis direction, thereby driving the first closure rod and the second closure rod to move in the second axis direction.

For example, the second threaded rod is further provided with an elastic member, and the elastic member is provided between the large bevel gear and the first threaded rod; and if the large bevel gear is engaged with the small bevel gear, the elastic member is compressed.

For example, the surgical instrument further comprises a safety switch serving as a stopper, the safety switch is provided on the closure assembly, the safety switch comprises a switching knob and a switching shaft, the switching shaft is connected to the switching knob, and the second closure rod is provided with a through hole adapted to the switching shaft; and if the suturing mechanism is closed, the switching knob is toggled, the switching shaft is inserted into the through hole to lock the closure assembly.

For example, the elastic member is a compression spring, and an adjusting nut is provided on the second threaded rod to fix the compression spring.

For example, the anvil assembly further comprises a lower jaw arm, the anvil is provided on the lower jaw arm, the lower jaw arm is provided with a slot hole for accommodating the first threaded rod and the firing nut, and the first threaded rod is fixed on the lower jaw arm by a first bearing.

For example, the surgical instrument further comprises a handle, the transmission rod is fixed to the handle by a second bearing, the drive assembly is provided in the handle, and the drive assembly comprises a drive motor, an input shaft connected to the drive motor, and a transmission member respectively connected to the input shaft and the transmission rod.

For example, the surgical instrument further comprises an induction switch for sensing a position of the staple cartridge assembly, and the induction switch is provided in the handle.

A linear surgical stapler is provided by the embodiments of the disclosure, which comprises the surgical instrument as described above and the staple cartridge assembly, and the staple cartridge assembly is mounted to the mounting part.

Compared with the prior art, the beneficial effects of the embodiments of the present disclosure at least are as follows. The surgical instrument and the linear surgical stapler of the embodiments of the present disclosure are provided with the staple pushing assembly and the direction-changing transmission device. If the suturing mechanism is closed, the direction-changing transmission device drives the first threaded rod in the staple pushing assembly to rotate, so that the firing nut sleeved on the first threaded rod moves relative to the first threaded rod in the first axis direction, and the staples in the staple cartridge are fired sequentially. Therefore, there is no problem such as large and small heads, dovetail and the like. In addition, the surgical instrument and the linear surgical stapler fire the staples sequentially, which can reduce the firing force to avoid the deformation of the anvil, and have a better insertion effect of the staples into the tissue, a better suturing effect and surgical safety.

The above description is only an outline of the technical solutions of the embodiments of the present disclosure. In order to better understand the technical solutions of the embodiments of the present disclosure so that they can be implemented according to the contents of the specification, the following detailed description will be made with the exemplary embodiments of the present disclosure in conjunction with the accompanying drawings.

DETAILED DESCRIPTION

The exemplary specific implemented modes of the present disclosure will be described in further detail below in conjunction with the drawings and embodiments. The following embodiments are intended to illustrate the present disclosure, but not to limit the scope of the present disclosure.

It should be noted that the terms such as "upper", "lower", "left", "right", "inner", "outer" and the like in the present disclosure are only intended to describe the embodiments of the present disclosure by referring to the drawings, and are not used as limiting terms.

Referring to FIGS. 1 to 5, a surgical instrument according to the embodiments of the present disclosure includes: a suturing mechanism (i.e. an end effector) that includes an anvil assembly 1 and a mounting part 101 for mounting a staple cartridge assembly 2, in which the mounting part 101 may be installed with the staple cartridge assemblies 2 of different specifications according to actual requirements, the staple cartridge assembly 2 includes a staple cartridge 21 for accommodating staples 23, and the anvil assembly 1 includes an anvil 11 matched with the staple cartridge 21; a staple pushing assembly 3 configured to push the staples 23 to move towards the anvil assembly 1, in which the staple pushing assembly 3 includes a first threaded rod 31 provided on the anvil assembly 1 and a firing nut 32 sleeved on the first threaded rod 31, and an axis direction of the threaded rod 31 and the firing nut 32 is defined as a first axis direction (i.e. a straight line of Arrow A in FIG. 2); a transmission assembly 4 connected to the staple cartridge assembly 2 to drive the staple cartridge assembly 2 to move relative to the anvil assembly; and a drive assembly 5 connected to the transmission assembly 4 to drive the transmission assembly 4 to move. The surgical instrument of the embodiments of the present disclosure further includes a direction-changing transmission device 6. If the suturing mechanism is closed, the direction-changing transmission device 6 connects the staple pushing assembly 3 and the transmission assembly 4 and drives the first threaded rod 31 to rotate, so that the firing nut 32 moves relative to the first threaded rod 31 in the first axis direction.

In the embodiments of the present disclosure, the surgical instrument of the embodiments of the present disclosure includes two plate pieces 10 as a main body of the surgical instrument. The suturing mechanism is provided at a distal end of the plate pieces 10 (in a direction indicated by Arrow B in FIG. 2). For example, the distal end of the plate pieces 10 is the mounting part 101. The mounting part 101 for example is a concave structure, the anvil 11 is provided on a left side of the concave structure, and the staple cartridge 21 is provided on a right side of the concave structure. The staple cartridge 21 comprises a staple pushing sheet 24 for accommodating and firing the staples 23. The structure of the staple pushing sheet 24 may refer to common design, which is not detailed here. The staple cartridge assembly 2 further includes a connecting part 22. The connecting part 22 connects the staple cartridge 21 and the mounting part 101. An upper tissue positioning needle 221 is provided in the connecting part 22. An upper tissue positioning hole 121 corresponding to the upper tissue positioning needle 221 is provided on the anvil assembly 1. If the suturing mechanism is closed, the upper tissue positioning needle 221 is inserted into the upper tissue positioning hole 121 to fix the tissue to be sutured. The anvil assembly 1 includes a front jaw arm 12 and a lower jaw arm 13. The front jaw arm 12 is provided on an outer side of the anvil 11 to protect and fix the anvil 11. The lower jaw arm 13 serves as a bottom of the concave structure. The anvil 11 is provided on the lower jaw arm 13. The lower jaw arm 13 is provided with a slot hole (not numbered) for accommodating the first threaded rod 31 and the firing nut 32. The first threaded rod 31 is fixed on the lower jaw arm 13 by a first bearing 131. A lower tissue positioning needle 122 is fixedly provided on the front jaw arm 12. The lower tissue positioning needle 122 is inserted into the staple cartridge assembly 2 if the suturing mechanism is closed.

In the embodiments of the present disclosure, the transmission assembly 4 includes a transmission rod 41. The transmission rod 41 is connected to the drive assembly 5 and rotates under the action of the drive assembly 5. An axis direction of the transmission rod 41 is defined as a second axis direction (a straight line of Arrow B in FIG. 2). The first axis direction is perpendicular to the second axis direction. In the embodiments of the present disclosure, the transmission rod 41 is provided between the two plate pieces 10. The transmission rod 41 is a second threaded rod. A threaded sleeve 42 and a sleeve 43 are sleeved on the second threaded rod 41. The threaded sleeve 42 is preferably provided at a middle portion of the second threaded rod 41. The sleeve 43 is connected to the threaded sleeve 42 and provided on a position close to a distal end of the second threaded rod 41. The drive assembly 5 drives the second threaded rod 41 to rotate, the threaded sleeve 42 moves relative to the second threaded rod 41 in the second axis direction so as to drive the sleeve 43 to move relative to the second threaded rod 41 in the second axis direction. In the embodiments of the present disclosure, the second threaded rod 41 for example is provided with threads only at the middle portion of the second threaded rod 41. If the suturing mechanism is closed, the threaded sleeve 42 is located at a distal end of the threads of the second threaded rod 41.

In the embodiments of the present disclosure, the direction-changing transmission device 6 includes a large bevel gear 61 sleeved on the second threaded rod 41 and a small bevel gear 62 sleeved on the first threaded rod 31. The large bevel gear 61 is provided on the distal end of the second threaded rod 41. The sleeve 43 is provided between the threaded sleeve 42 and the large bevel gear 61. The drive assembly 5 drives the second threaded rod 41 to rotate, the threaded sleeve 42 drives the sleeve 43 to move toward the distal end of the second threaded rod 41, the sleeve 43 abuts against the large bevel gear 61 and pushes the large bevel gear 61 to move towards the small bevel gear 62; if the suturing mechanism is closed, the large bevel gear 61 and the small bevel gear 62 are engaged with each other, at this time, because the second threaded rod 41 rotates under the action of the drive assembly 5, the large bevel gear 61 follows the second threaded rod 41 to rotate with respect to the second axis direction, the large bevel gear 61 drives the small bevel gear 62 and the first threaded rod 31 to rotate with respect to the first axis direction, so that the firing nut 32 sleeved on the first threaded rod 31 moves upward relative to the first threaded rod 31 in the first axis direction, and the firing nut 32 pushes the staple pushing sheet 24 from bottom to top to sequentially fire the staples. After the firing of the staples is completed, the firing nut 32 returns to its initial position.

In the embodiments of the present disclosure, an elastic member 411 is further provided on the second threaded rod 41. The elastic member 411 is provided between the large bevel gear 61 and the first threaded rod 31. If the large bevel gear 61 and the small bevel gear 62 are engaged with each other, the elastic member 411 is compressed. If the firing of the staples is completed, the second threaded rod 41 rotates reversely under the action of the drive assembly 5, and drives the threaded sleeve 42 and the sleeve 43 to retreat toward a proximal end of the second threaded rod 41; at this time, the large bevel gear 61 is pushed back to its initial position under a recovering elastic force of the elastic member 411. Preferably, the elastic member 411 is a compression spring. An adjusting nut 412 is provided at the distal end of the second threaded rod 41 to fix the compression spring 411. In the embodiments of the present disclosure, the threaded sleeve 42 and the sleeve 43 are integral with each other, or are separately provided and then connected together. Preferably, the threaded sleeve 42 and the sleeve 43 are integral with each other.

In the embodiments of the present disclosure, the transmission assembly 4 further includes a closure assembly 44 sleeved on the second threaded rod 41. The closure assembly 44 includes a first closure rod 441 and a second closure rod 442. The threaded sleeve 42 is fixedly connected to the first closure rod 441 and the second closure rod 442. The threaded sleeve 42 is provided between the first closure rod 441 and the second closure rod 442. For example, the first closure rod 441 is connected to the connecting part 22 of the staple cartridge assembly 2. The second closure rod 442 is provided closer to the drive assembly than the first closure rod 441 (i.e. the second closure rod 442 is at a proximal end). The drive assembly 5 drives the second threaded rod 41 to rotate, the threaded sleeve 42 moves relative to the second threaded rod 41 in the second axis direction, thereby driving the first closure rod 441 and the second closure rod 442 to move in the second axis direction. The first closure rod 441 is connected to the staple cartridge assembly 2, so that during the threaded sleeve 42 moves toward the distal end of the second threaded rod 41, the first closure rod 441 pushes the staple cartridge assembly 2 to move toward the anvil 11 to close the suturing mechanism. The first closure rod 441 and the second closure rod 442 are integral with each other, or are provided separately and then connected together. Preferably, the first closure rod 441 and the second closure rod 442 are integral with each other, and are provided with a slot hole (not shown) for accommodating the threaded sleeve 42.

In the embodiments of the present disclosure, a protruding rod 4411 is provided on the first closure rod 441. The protruding rod 4411 abuts against a proximal end of the upper tissue positioning needle 221. During the first closure rod 441 drives the staple cartridge assembly 2 to move toward the anvil 11, the protruding rod 4411 drives the upper tissue positioning needle 221 to move toward the upper tissue positioning hole 121 and insert into the upper tissue positioning hole 121, so that the tissue to be sutured is positioned by the upper tissue positioning needle 221 so as to facilitate subsequent suturing and cutting.

The surgical instrument of the embodiments of the present disclosure further includes a safety switch 7 serving as a stopper. The safety switch 7 is provided on the closure assembly 44. For example, the safety switch 7 includes a switching knob 71 and a switching shaft 73. The switching shaft 73 is connected to the switching knob 71. A through hole 72 adapted to the switching shaft 73 is provided on the second closure rod 442. After the suturing mechanism is closed, the switching knob 71 is toggled to insert the switching shaft 73 into the through hole 72 to lock the closure assembly 44. The safety switch 7 may refer to common design, which is not detailed here.

The surgical instrument of the embodiments of the present disclosure further includes a handle 100. The transmission rod 41 is fixed to the handle 100 by a second bearing 413. The second closure rod 442 and the drive assembly 5 are fixed to the handle 100. A manner of fixing may refer to common manner, such as a thread connection manner, a bonding manner, or a snap connection manner, which is not limited herein. The drive assembly 5 includes a drive motor 50, an input shaft 51 connected to the drive motor 50, and a transmission member 52 respectively connected to the input shaft 51 and the transmission rod 41. The transmission member 52 includes a first bevel gear 521 sleeved on the input shaft 51 and a second bevel gear 522 sleeved on the transmission rod 41. The first bevel gear 521 is engaged with the second bevel gear 522 to transform a rotation of the input shaft 51 with respect to the first axis direction into a rotation of the transmission rod 41 with respect to the second axis direction.

In the embodiments of the present disclosure, the surgical instrument further includes an induction switch 200 for sensing the position of the staple cartridge assembly 2. The induction switch 200 is fixed in the handle 100; and a manner of fixing may refer to common design, such as the thread connection manner, the bonding manner, or the snap connection manner, which is not limited herein. The induction switch 200 is a Hall switch or a photoelectric switch. Upon the large bevel gear 61 is engaged with the small bevel gear 62 in the suturing mechanism, the staple cartridge assembly 2 at this time is provided at a position that the staple cartridge 21 and the anvil 11 are closed together, and the position of the staple cartridge assembly 2 is acquired by the induction switch 200.

In the embodiments of the present disclosure, a plugging hole for external power (not shown), a step indicator (not shown), and an operation button (not shown) are also provided on the handle 100. The plugging hole for example is connected to a power line of a medical power supply. Of course, the instrument may be powered by a built-in power supply, such as a battery.

Preferably, the surgical instrument of the embodiments of the present disclosure is a linear surgical stapler, and the staple cartridge assembly 2 is mounted on the mounting part 101 of the linear surgical stapler.

The linear surgical stapler operates as follows.

Figure 1:
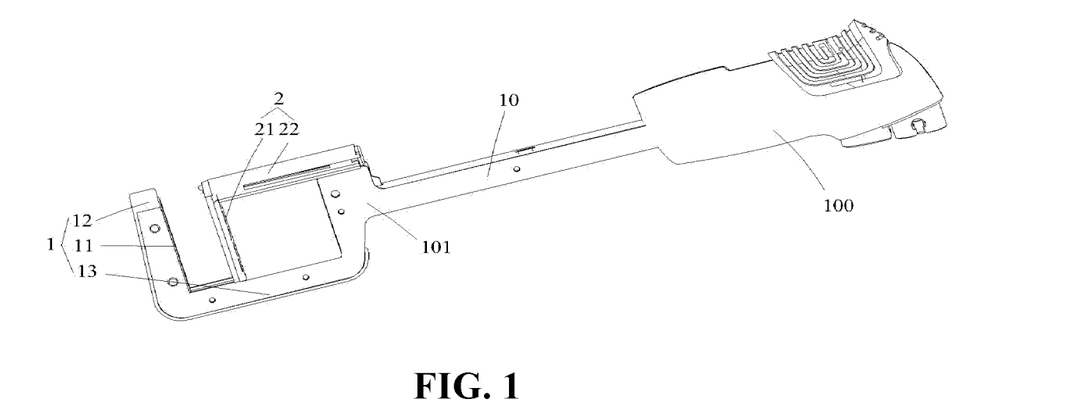
FIG. 1 is a schematic diagram of an external structure of a surgical instrument according to embodiments of the present disclosure.
Figure 2:
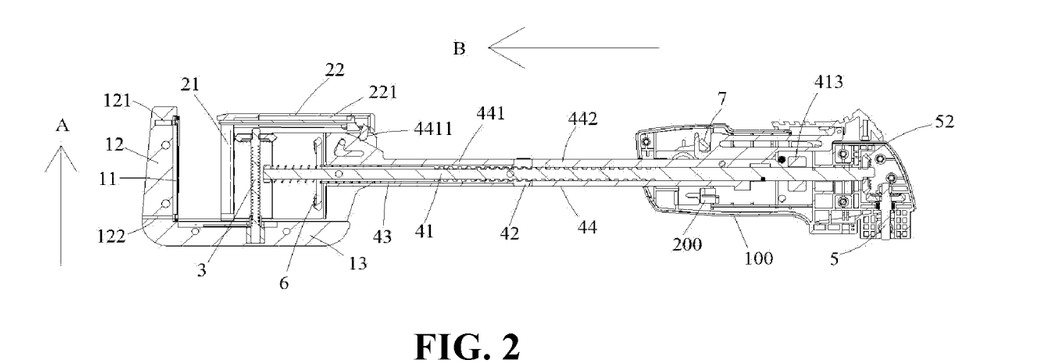
FIG. 2 is a schematic diagram of an overall structure of the surgical instrument according to the embodiments of the present disclosure.
Figure 3:
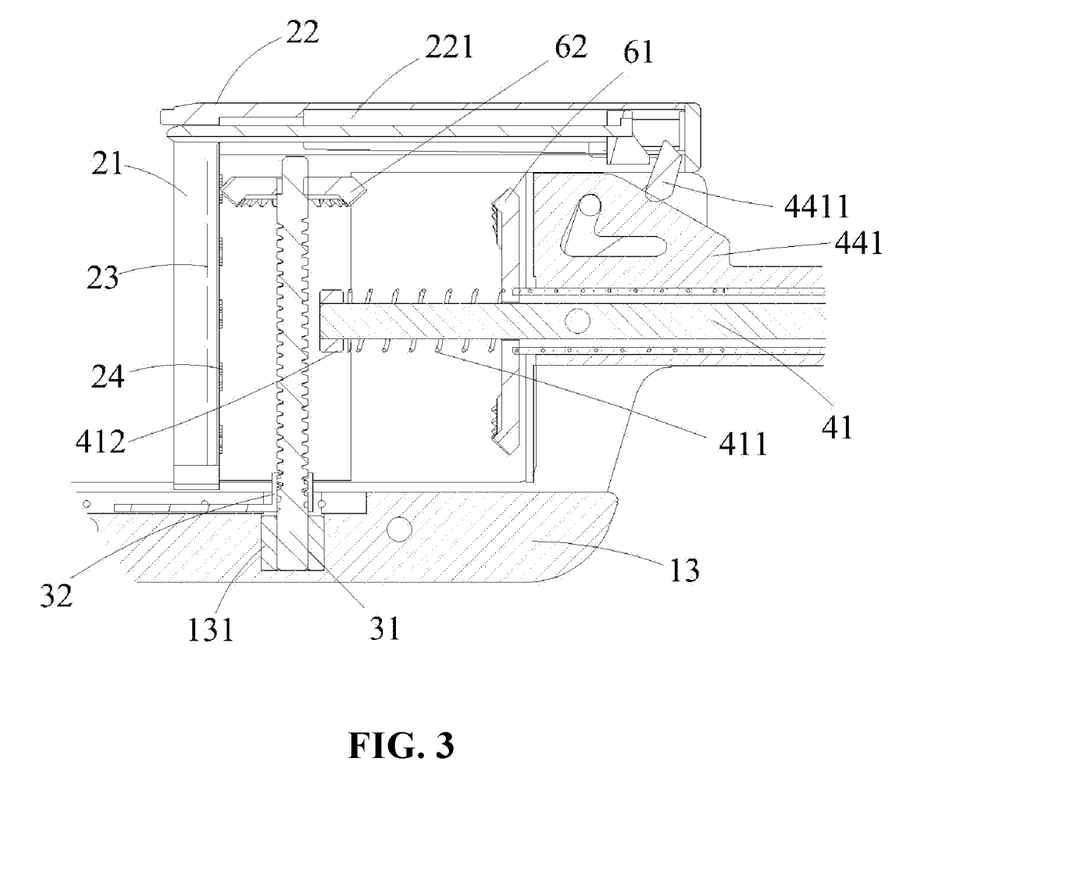
FIG. 3 is a schematic diagram of a distal end of the surgical instrument according to the embodiments of the present disclosure.
Figure 4:
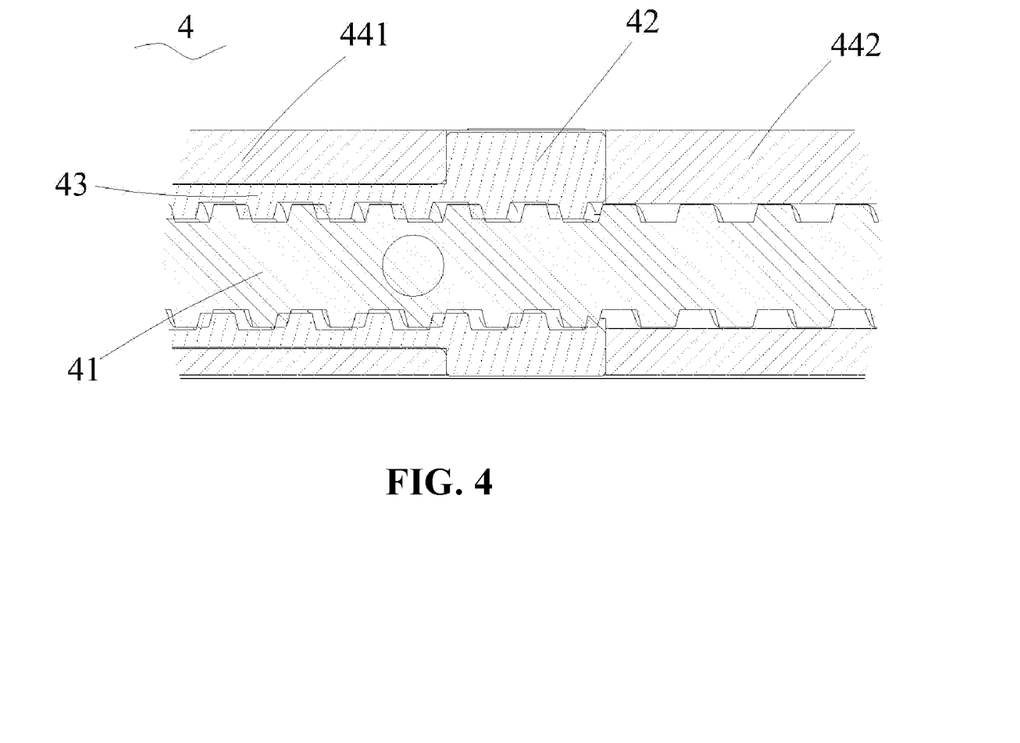
FIG. 4 is a schematic structural diagram of a transmission assembly of the surgical instrument according to the embodiments of the present disclosure.
Figure 5:
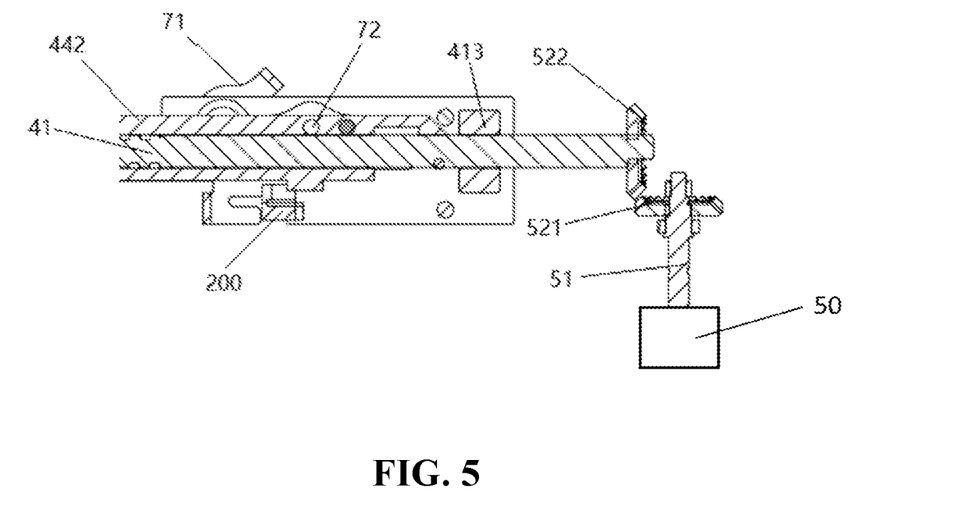
FIG. 5 is a schematic structural diagram of a proximal end of the surgical instrument according to the embodiments of the present disclosure.
Figure 6:
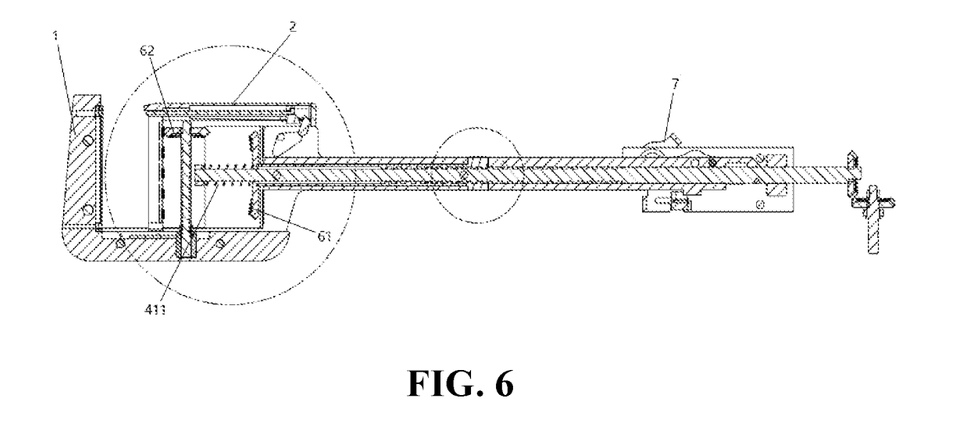
FIG. 6 is a schematic structural diagram of a linear surgical stapler in an initial state according to the embodiments of the present disclosure.
Figure 7:
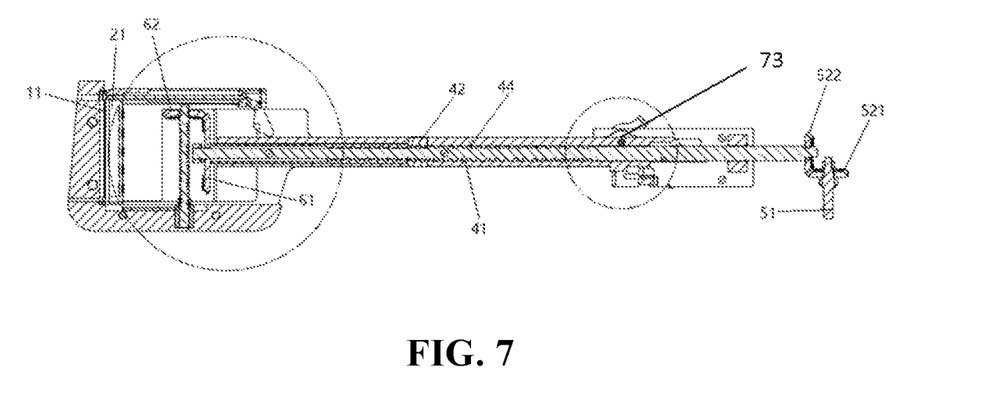
FIG. 7 is a schematic structural diagram of the linear surgical stapler in a closed state according to the embodiments of the present disclosure.
Figure 8:
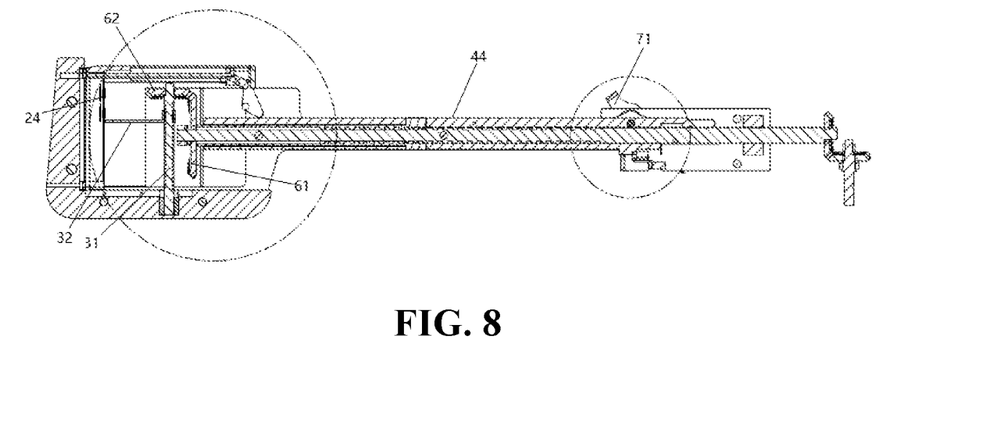
FIG. 8 is a schematic structural diagram of the linear surgical stapler in a firing state according to the embodiments of the present disclosure.

Referring to FIG. 6, in an initial state, the staple cartridge assembly 2 is spaced from the anvil assembly 1, at this time, the safety switch 7 is in an "open" state, the large bevel gear 61 is spaced from the small bevel gear 62, and the compression spring 411 is in a free state. Referring to FIG. 7, the operation button on the handle is pressed, and the drive motor 50 is driven to drive the input shaft 51 to rotate; due to the engagement between the first bevel gear 521 and the second bevel gear 522, the second threaded rod 41 is driven to rotate, thereby driving the threaded sleeve 42 sleeved on the second threaded rod 41 to push the closure assembly 44 and the large bevel gear 61 to move toward to the distal end of the second threaded rod 41 until the large bevel gear 61 is engaged with the small bevel gear 62, at this time, the compression spring 411 is compressed, the staple cartridge 21 is at the position that the staple cartridge 21 and the anvil 11 are closed together to clamp the target tissue to be sutured, the position of the staple cartridge 21 is acquired by the induction switch 200 (such as the photoelectric switch), and the suturing mechanism is in a closed state (i.e. a state in which the target tissue is clamped by the staple cartridge 21 and the anvil 11). Referring to FIG. 8, after the suturing mechanism is in the closed state, the switching knob 71 is toggled so that the safety switch 7 is in a "locked" state, at this time, the closure assembly 44 is locked; then, the drive motor 50 continues to rotate, the large bevel gear 61 and the small bevel gear 62 are engaged with each other to drive the first threaded rod 31 to rotate, the first threaded rod 31 drives the firing nut 32 to move upward in the first axis direction, thereby pushing the staple pushing sheet 24 to sequentially fire the staples. After the firing of the staples is completed, the firing nut 32 automatically returns to an initial position. After the firing of the staples is completed, the safety switch is turned back to the "open" state, the drive motor 50 rotate reversely, the second threaded rod 41 rotate reversely to drive the closure assembly 44 to move back so that a distance between the staple cartridge assembly 2 and anvil assembly 1 restores to the maximum (which may be controlled by the number of turns of the drive motor 50), which is consistent with the initial state.

In summary, the surgical instrument and the linear surgical stapler of the embodiments of the present disclosure are provided with the staple pushing assembly and the direction-changing transmission device. If the suturing mechanism is closed, the direction-changing transmission device drives the first threaded rod in the staple pushing assembly to rotate, so that the firing nut sleeved on the first threaded rod moves relative to the first threaded rod in the first axis direction, and the staples in the staple cartridge are fired sequentially. Therefore, there is no problem such as large and small heads, dovetail and the like. In addition, the surgical instrument and the linear surgical stapler fire the staples sequentially, which can reduce the firing force to avoid the deformation of the anvil, and have a better insertion effect of the staples into the tissue, a better suturing effect and surgical safety.

The technical features of the foregoing embodiments may be combined arbitrarily. In order to make the description concise, all possible combinations of the various technical features in the foregoing embodiments are not described. However, as long as there is no conflict in the combination of these technical features, all combinations should be considered as within the scope of the disclosure.

The foregoing embodiments merely are some of the embodiments of the present disclosure and the descriptions of the foregoing embodiments are specific and detailed, but the foregoing embodiments should not be understood as limiting of the scope of the disclosure. It should be pointed out that a person of ordinary skill in the art may make modifications and improvements without departing from the concept of the present disclosure, and all of these modifications and improvements belong to the protection scope of the present disclosure. Therefore, the protection scope of the present disclosure should be defined by the appended claims.

What is claimed is:

1. A surgical instrument, comprising:
a staple cartridge assembly;
a suturing mechanism comprising an anvil assembly and a mounting part, the staple cartridge assembly is mounted on the mounting part, wherein the staple cartridge assembly comprises a staple cartridge for accommodating staples, and a connecting part, and the anvil assembly comprises an anvil cooperated with the staple cartridge;
a staple pushing assembly configured to push the staples so that the staples are sequentially fired;
a transmission assembly configured for driving the staple cartridge assembly to move relative to the anvil assembly and driving the staple pushing assembly to move to push the staples; and
a drive assembly connected to the transmission assembly and configured for driving the transmission assembly to move,
wherein the staple pushing assembly comprises a first threaded rod provided on the anvil assembly and a firing nut sleeved on the first threaded rod, and an axis direction of the first threaded rod and the firing nut is defined as a first axis direction;

wherein the surgical instrument further comprises a direction-changing transmission device:

if the suturing mechanism is closed, the direction-changing transmission device connects the staple pushing assembly and the transmission assembly and drives the first threaded rod to rotate, so that the firing nut moves relative to the first threaded rod in the first axis direction;

wherein the transmission assembly comprises a transmission rod, the transmission rod is connected to the drive assembly and rotates under an action of the drive assembly, an axis direction of the transmission rod is defined as a second axis direction, and the first axis direction is perpendicular to the second axis direction;

wherein the direction-changing transmission device comprises a large bevel gear sleeved on the transmission rod and a small bevel gear sleeved on the first threaded rod; and if the suturing mechanism is closed, the large bevel gear is engaged with the small bevel gear;

wherein the transmission rod is a second threaded rod, a threaded sleeve and a sleeve are sleeved on the second threaded rod, and the sleeve is connected to the threaded sleeve and provided between the threaded sleeve and the large bevel gear; and if the drive assembly drives the second threaded rod to rotate, the threaded sleeve moves relative to the second threaded rod in the second axis direction, thereby driving the sleeve to move relative to the second threaded rod in the second axis direction;

wherein the second threaded rod is further provided with an elastic member, and the elastic member is provided between the large bevel gear and the first threaded rod; and if the large bevel gear is engaged with the small bevel gear, the elastic member is compressed.

2. The surgical instrument of claim 1, wherein the transmission assembly further comprises a closure assembly sleeved on the second threaded rod, the closure assembly comprises a first closure rod and a second closure rod, the threaded sleeve is fixedly connected to the first closure rod and the second closure rod, and the threaded sleeve is provided between the first closure rod and the second closure rod in the second axis direction;

the first closure rod is connected to the connecting part of the staple cartridge assembly, and the second closure rod is provided closer to the drive assembly than the first closure rod; and if the drive assembly drives the second threaded rod to rotate, the threaded sleeve moves relative to the second threaded rod in the second axis direction, thereby driving the first closure rod and the second closure rod to move in the second axis direction.

3. The surgical instrument according to claim 2, wherein the surgical instrument further comprises a safety switch serving as a stopper, the safety switch is provided on the closure assembly, the safety switch comprises a switching knob and a switching shaft, the switching shaft is connected to the switching knob, and the second closure rod is provided with a through hole adapted to the switching shaft; and if the suturing mechanism is closed, the switching knob is toggled, the switching shaft is inserted into the through hole to lock the closure assembly.

4. The surgical instrument according to claim 1, wherein the anvil assembly further comprises a lower jaw arm, the anvil is provided on the lower jaw arm, and the first threaded rod is fixed on the lower jaw arm.

5. The surgical instrument according to claim 4, wherein the anvil assembly further includes a front jaw arm, and the front jaw arm is provided on an outer side of the anvil to protect and fix the anvil.

6. The surgical instrument according to claim 5, wherein a lower tissue positioning needle is fixedly provided on the front jaw arm, and the lower tissue positioning needle is inserted into the staple cartridge assembly if the suturing mechanism is closed.

7. The surgical instrument according to claim 1, wherein the surgical instrument further comprises a handle, the transmission rod is fixed to the handle, the drive assembly is provided in the handle, and the drive assembly comprises a drive motor, an input shaft connected to the drive motor, and a transmission member respectively connected to the input shaft and the transmission rod.

8. The surgical instrument according to claim 7, wherein the surgical instrument further comprises an induction switch for sensing a position of the staple cartridge assembly, and the induction switch is provided in the handle.

9. The surgical instrument according to claim 7, wherein the transmission member includes a first bevel gear sleeved on the input shaft and a second bevel gear sleeved on the transmission rod, and the first bevel gear is engaged with the second bevel gear to transform a rotation of the input shaft with respect to the first axis direction into a rotation of the transmission rod with respect to the second axis direction.

10. A linear surgical stapler, comprising the surgical instrument according to claim 1.

11. The surgical instrument according to claim 7, wherein the connecting part connects the staple cartridge and the mounting part;

an upper tissue positioning needle is provided in the connecting part, an upper tissue positioning hole corresponding to the upper tissue positioning needle is provided on the anvil assembly; and a protruding rod is provided on the first closure rod, and during the first closure rod drives the staple cartridge assembly to move toward the anvil, the protruding rod drives the upper tissue positioning needle to move toward the upper tissue positioning hole and insert into the upper tissue positioning hole.

12. The surgical instrument according to claim 1, wherein the surgical instrument further includes two plate pieces as a main body of the surgical instrument, the suturing mechanism is provided at a distal end of the two plate pieces, and the transmission rod is provided between the two plate pieces.

13. The surgical instrument according to claim 1, wherein the second threaded rod is provided with threads only at a middle portion of the second threaded rod; and if the suturing mechanism is closed, the threaded sleeve is located at a distal end of the threads of the second threaded rod.

* * * * *

UNITED STATES PATENT AND TRADEMARK OFFICE
CERTIFICATE OF CORRECTION

| | |
|---|---|
| PATENT NO. | : 11,497,500 B2 |
| APPLICATION NO. | : 17/273057 |
| DATED | : November 15, 2022 |
| INVENTOR(S) | : Xu et al. |

It is certified that error appears in the above-identified patent and that said Letters Patent is hereby corrected as shown below:

In the Claims

In Column 10, Line 38 in Claim 11, delete "7" and insert therefor --1--.

Signed and Sealed this
Fourteenth Day of March, 2023

Katherine Kelly Vidal
*Director of the United States Patent and Trademark Office*